United States Patent [19]
Kanne et al.

[11] Patent Number: 5,714,438
[45] Date of Patent: Feb. 3, 1998

[54] HERBICIDAL 5-SUBSTITUTED PYRIMIDINE COMPOUNDS AND DERIVATIVES THEREOF

[75] Inventors: David B. Kanne, Corte Madera; Michael P. Prisbylla, Pleasant Hill, both of Calif.

[73] Assignee: Zeneca Limited, London, England

[21] Appl. No.: 761,620

[22] Filed: Dec. 5, 1996

Related U.S. Application Data

[63] Continuation-in-part of Ser. No. 475,914, Jun. 7, 1995, abandoned.

[51] Int. Cl.$^6$ .................. C07D 403/02; A01N 43/54
[52] U.S. Cl. .................. 504/239; 504/242; 504/243; 544/60; 544/123; 544/122; 544/296
[58] Field of Search ............... 544/296, 60, 122, 544/123; 504/239, 242, 243

[56] References Cited

U.S. PATENT DOCUMENTS 5,595,958  1/1997  Chin et al. .................. 504/250

OTHER PUBLICATIONS

R. Radinov et al., Synthesis of 4-Amino-3-pyridinyl and 4-Amino-5 pyrimidinyl Aryl Ketones and Related Compounds via an ortho-Lithiation Reaction, Synthesis, 886-891 (1986).

Ple et al., Journal of Heterocyclic Chemistry, 28(2), 283-287, Feb. 1991.

*Primary Examiner*—Matthew V. Grumbling
*Attorney, Agent, or Firm*—Joseph R. Snyder

[57] ABSTRACT

Herbicidal 5-substituted pyrimidine compounds and derivatives thereof of the formula:

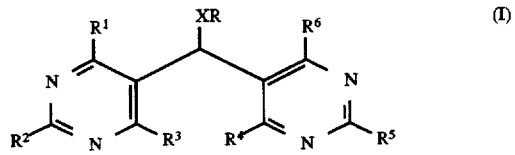

Herbicidal compositions containing such 5-substituted pyrimidine compounds and derivatives thereof and methods of controlling undesirable vegetation using these compounds and derivatives are also disclosed. The compounds in which XR is hydroxyl are also useful as intermediates for producing the 5-substituted pyrimidine derivatives of the invention.

3 Claims, No Drawings

HERBICIDAL 5-SUBSTITUTED PYRIMIDINE COMPOUNDS AND DERIVATIVES THEREOF

CROSS REFERENCE TO RELATED APPLICATION

This is a continuation-in-part of U.S. application Ser. No. 08/475,914, filed Jun. 7, 1995, now abandoned.

FIELD OF THE INVENTION

In one aspect, this invention relates to novel 5-substituted pyrimidine compounds and derivatives thereof which exhibit unexpectedly desirable herbicidal activity. In other aspects, this invention relates to herbicidal compositions containing a 5-substituted pyrimidine compound or derivative thereof and an agriculturally acceptable carrier, to a method of controlling undesirable vegetation by applying to an area where control is desired an herbicidally effective mount of a 5-substituted pyrimidine compound or derivative thereof and to intermediates useful in making such compounds.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on non-cropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds. Further, it is an object of this invention to provide intermediates which, as well as exhibiting herbicidal activity, are also useful in the production of other herbicidally active compounds.

SUMMARY OF THE INVENTION

In one aspect, this invention is directed to compounds of formula (I):

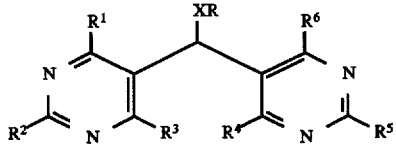

wherein:

$R^1$, $R^2$, $R^3$, $R^4$, $R^5$ and $R^6$ are each independently hydrogen, halogen, $C_1$–$C_6$ alkyl, $C_2$–$C_6$ alkenyl, $C_2$–$C_6$ alkynyl, ($C_1$–$C_6$)alkyl($C_3$–$C_6$)cycloalkyl, nitro, cyano, hydroxy, thiocyano, —N($R^7$)($R^8$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(Z)—$R^9$ or —S(O)$_m$—$R^{10}$, wherein $R^7$ and $R^8$ are each independently $C_1$–$C_6$ alkyl, $C_1$–$C_6$ alkylthio or $C_1$–$C_6$ alkoxy, $R^9$ and $R^{10}$ are each independently hydrogen, $C_1$–$C_6$ alkyl or phenyl, Z is oxygen or sulfur and m is 0, 1 or 2;

X is oxygen or sulfur;

R is hydrogen, hydrocarbyl, hydrocarbyl substituted with one or more of halogen or $C_1$–$C_6$ alkoxy or R is of the formula —C(Y)—$R^{11}$, —C(O)—C(O)—$R^{11}$, —S(O)$_2$—$R^{11}$, —P(Y)($R^{12}$)($R^{13}$) or —Si($R^{14}$)($R^{15}$)($R^{16}$); wherein Y is oxygen or sulfur;

$R^{11}$ is hydrocarbyl, substituted hydrocarbyl, hydrocarbyloxy, substituted hydrocarbyloxy, hydrocarbyl—S—, substituted hydrocarbyl—S— or is of the formula —N($R^{17}$)($R^{18}$), wherein $R^{17}$ and $R^{18}$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl ($C_1$–$C_6$)alkyl, hydroxycarbonyl($C_1$–$C_6$)alkyl, or N($R^{19}$)($R^{20}$) wherein $R^{19}$ and $R^{20}$ are each independently hydrogen, $C_1$–$C_6$ alkyl or phenyl;

or $R^{17}$ and $R^{18}$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolodine ring, any of which may be optionally substituted with $C_1$–$C_6$ alkyl;

$R^{12}$ and $R^{13}$ are each independently $C_1$–$C_6$ alkyl, $C_1$–$C_6$ alkylthio or $C_1$–$C_6$ alkoxy;

$R^{14}$, $R^{15}$ and $R^{16}$ are each independently $C_1$–$C_6$ alkyl, $C_1$–$C_6$ alkoxy, $C_1$–$C_6$ haloalkyl, aryl or arylalkyl;

or an N-oxide thereof, and agriculturally acceptable salts thereof; with the proviso that when $R^1$ and $R^6$ are chloro and $R^2$, $R^3$, $R^4$ and $R^5$ are methoxy then R is not hydrogen.

In another aspect, this invention is directed to an herbicidal composition containing (A) a compound of formula (I)

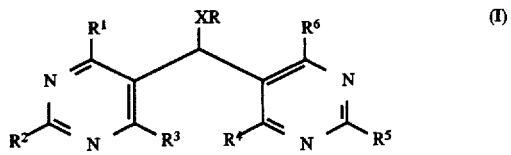

wherein $R^1$, $R^2$, $R^3$, $R^4$, $R^5$, $R^6$, X and R have the same meanings as above, or an N-oxide thereof, or an agriculturally acceptable salt thereof; and (B) a carrier therefor.

In still another aspect, this invention is directed to a method for controlling undesirable vegetation by applying to an area where such vegetation control is desired an herbicidally effective amount of a compound of formula (I), or an N-oxide thereof:

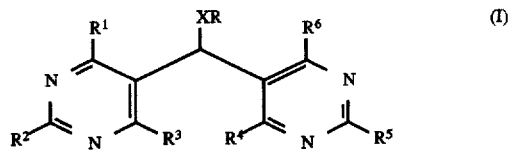

wherein $R^1$, $R^2$, $R^3$, $R^4$, $R^5$, $R^6$, X and R have the same meanings as above, or an agriculturally acceptable salt thereof.

In yet a further aspect, because the compounds of this invention wherein XR is OH are useful intermediates for producing other compounds of this invention, as well as possessing herbicidal activity, this invention is directed to compounds of formula (Ia), and N-oxides thereof:

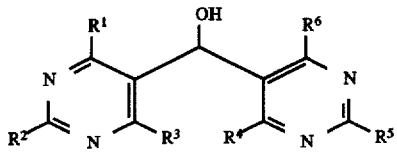

wherein $R^1$, $R^2$, $R^3$, $R^4$, $R^5$ and $R^6$ have the same meanings as in formula (I).

DETAILED DESCRIPTION OF THE INVENTION

The novel herbicidal compounds of this invention are of the formula (I):

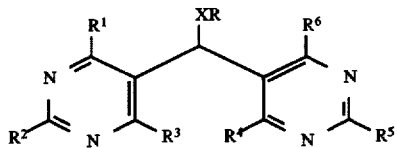

wherein:

$R^1$, $R^2$, $R^3$, $R^4$, $R^5$ and $R^6$ are each independently hydrogen, halogen, $C_1$–$C_6$ alkyl, $C_2$–$C_6$ alkenyl, $C_2$–$C_6$ alkynyl, $(C_1$–$C_6)$alkyl$(C_3$–$C_6)$cycloalkyl, nitro, cyano, hydroxy, thiocyano, —N($R^7$)($R^8$), $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, halo$(C_1$–$C_6)$alkoxy-$(C_1$–$C_6)$alkyl, —C(Z)—$R^9$ or —S(O)$_m$—$R^{10}$, wherein $R^7$ and $R^8$ are each independently $C_1$–$C_6$ alkyl, $C_1$–$C_6$ alkylthio or $C_1$–$C_6$ alkoxy, $R^9$ and $R^{10}$ are each independently hydrogen, $C_1$–$C_6$ alkyl or phenyl, Z is oxygen or sulfur and m is 0, 1 or 2;

X is oxygen or sulfur;

R is hydrogen, hydrocarbyl, hydrocarbyl substituted with one or more of halogen or $C_1$–$C_6$ alkoxy or R is of the formula —C(Y)—$R^{11}$, —C(O)—C(O)—$R^{11}$, —S(O)$_2$—$R^{11}$, —P(Y)($R^{12}$)($R^{13}$) or —Si($R^{14}$)($R^{15}$)($R^{16}$); wherein Y is oxygen or sulfur;

$R^{11}$ is hydrocarbyl, substituted hydrocarbyl, hydrocarbyloxy, substituted hydrocarbyloxy, hydrocarbyl-S—, substituted hydrocarbyl-S— or is of the formula —N($R^{17}$)($R^{18}$), wherein $R^{17}$ and $R^{18}$ are each independently hydrogen, hydrocarbyl, substituted hydrocarbyl, hydrocarbyloxy, substituted hydrocarbyloxy, pyridyl, furyl, thienyl, $(C_1$–$C_6)$alkoxycarbonyl $(C_1$–$C_6)$alkyl, hydroxycarbonyl$(C_1$–$C_6$ )alkyl, or N($R^{19}$)($R^{20}$) wherein $R^{19}$ and $R^{20}$ are each independently hydrogen, $C_1$–$C_6$ alkyl or phenyl;

or $R^{17}$ and $R^{18}$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolodine ring, any of which may be optionally substituted with $C_1$–$C_6$ alkyl;

$R^{12}$ and $R^{13}$ are each independently $C_1$–$C_6$ alkyl, $C_1$–$C_6$ alkylthio or $C_1$–$C_6$ alkoxy;

$R^{14}$, $R^{15}$ and $R^{16}$ are each independently $C_1$–$C_6$ alkyl, $C_1$–$C_6$ alkoxy, $C_1$–$C_6$ haloalkyl, aryl or arylalkyl;

and N-oxides thereof, and agriculturally acceptable salts thereof; with the proviso that when $R^1$ and $R^6$ are chloro and $R^2$, $R^3$, $R^4$ and $R^5$ are methoxy then R is not hydrogen.

Preferably, $R^1$, $R^2$, $R^3$, $R^4$, $R^5$ and $R^6$ are each independently hydrogen, halogen, $C_1$–$C_6$ alkyl, $C_1$–$C_6$ haloalkyl, $C_1$–$C_6$ alkoxy, $C_1$–$C_6$ haloalkoxy, nitro or —S(O)$_m$— $(C_1$–$C_3$ alkyl), wherein m is 0, 1 or 2, with at least one of $R^1$, $R^2$, $R^3$, $R^4$, $R^5$ and $R^6$ not being hydrogen; X is oxygen; and R is —C(O)—$R^{11}$, wherein $R^{11}$ is $C_1$–$C_{12}$ alkyl, $C_1$–$C_6$ haloalkyl, phenyl or is N($R^{17}$)($R^{18}$), wherein $R^{17}$ and $R^{18}$ are each independently $C_1$–$C_{12}$ alkyl, hydrogen, $C_2$–$C_{12}$ alkenyl, $C_2$–$C_{12}$ alkynyl, $C_1$–$C_{12}$ haloalkyl, $C_1$–$C_6$ alkoxy, $(C_1$–$C_6)$-alkoxy$(C_1$–$C_6$ )alkyl or $R^{17}$ and $R^{18}$ together with the nitrogen to which they are bound form a morpholine, piperidine or pyrrolidine ring. More preferably, $R^2$, $R^3$, $R^4$ and $R^5$ are hydrogen and $R^1$ and $R^6$ are each independently $C_1$–$C_6$ alkyl, $C_1$–$C_6$ haloalkyl, $C_1$–$C_6$ alkoxy or $C_1$–$C_3$ alkylthio.

The formulae given above are intended to include tautomeric forms of the structures drawn therein, as well as physically distinguishable modifications of the compounds which may arise, for example, from different ways in which the molecules are arranged in a crystal lattice, or form the inability of parts of the molecule to rotate freely in relation to other parts, or from geometrical isomerism, or from intramolecular or intermolecular hydrogen bonding, or otherwise.

The compounds of such formulae can exist in enantiomeric forms. This invention includes both individual enantiomers and mixtures of the two in all proportions.

As employed herein, the term "hydrocarbyl," whether representing a substituent on its own or whether it is part of the definition of a larger group (e.g., as in hydrocarbyloxy, hydrocarbyl-S(O)$_m$—, etc.) is intended to include hydrocarbyl groups having from 1 to 12 carbon atoms. The term hydrocarbyl, therefore, includes, for example, $C_1$ to $C_{12}$ alkyl including both straight and branched chain isomers (e.g., methyl, ethyl, propyl and hexyl); cycloalkyl of 3 to 12 carbon atoms (e.g., cyclopropyl, cyclobutyl and cyclohexyl); $C_2$ to $C_{12}$ alkenyl (e.g., allyl and crotyl); $C_2$ to $C_{12}$ alkynyl (e.g., propynyl); phenyl; phenylalkyl; alkylphenyl; alkenylphenyl; alkynylphenyl; benzyl; alkylbenzyl; alkenylbenzyl; alkynylbenzyl; naphthyl; and the like.

The term "substituted hydrocarbyl" is intended to include hydrocarbyl groups, as defined above, having one or more of the following substituents: halogen (i.e., fluorine, chlorine, bromine and iodine); $C_1$–$C_4$ alkoxy; $C_1$–$C_4$ alkyl-S(O)$_m$—; nitro; cyano; carboxy and salts, amides and esters thereof; alkanoyl of 2 to 4 carbon atoms; and phenyl optionally substituted with one or more $C_1$–$C_4$ alkyl, $C_1$–$C_4$ alkoxy, $C_1$–$C_4$ alkyl-S(O)$_m$—, nitro, halogen, fluorine, chlorine, bromine, cyano, or $CF_3$ groups. In the above definitions, m is 0, 1 or 2.

The expression "salts, amides and esters thereof" used above in relation to carboxy substitution includes, for example, salts formed from alkali metals (e.g., sodium, potassium and lithium), alkaline earth metals (e.g., calcium and magnesium), the ammonium ion and substituted ammonium ions wherein one, two, three or four of the hydrogen atoms have been replaced by optionally substituted $C_1$–$C_6$ hydrocarbyl moieties as defined above.

In the above definitions, the term "halogen" includes fluoro, chloro, bromo and iodo groups. In polyhalogenated groups, the halogens may be the same or different.

Particularly preferred compounds include:

1-(4-trifluoromethylpyrimidin-5-yl)-1-(4-methylpyrimidin-5-yl)-1-benzyloxymethane;

1,1-bis-(4-trifluoromethylpyrimidin-5-yl)-1-benzyloxymethane;

1,1-bis-(4-trifluoromethylpyrimidin-5-yl)-1-(4-fluorobenzyloxy)methane;

1-(4-(2-trifluoro-1-difluoro)ethylpyrimidin-5-yl)-1-(4-methylpyrimidin-5-yl)-1-trimethylacetoxymethane; and 1-(4-trifluoromethylpyrimidin-5-yl)-1-(4-methoxypyrimidin-5-yl)-1-benzyloxymethane.

The compounds of the present invention have been found to be active herbicides, possessing utility as pre-emergence and post-emergence herbicides. These compounds are useful against a wide range of plant species including broadleaf, grassy and perennial species.

This invention, therefore, also relates to a method for controlling undesirable vegetation comprising applying to a locus where control of such vegetation is desired, either prior or subsequent to the emergence of such vegetation, an herbicidally effective amount of a compound of formula (I) hereof, together with an agriculturally acceptable inert diluent or carrier suitable for use with herbicides.

The terms "herbicide" and "herbicidal" are used herein to denote the inhibitive control or modification of undesired plant growth. Inhibitive control and modification include all deviations from natural development, such as, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalide, acetic, sulfonic, phosphonic, inorganic and organic acid salts.

In general, the compounds of this invention are prepared by (A) reacting a substituted pyrimidine compound with a substituted or unsubstituted pyrimidine carboxaldehyde in the presence of a suitable base to form a 5-substituted pyrimidine compound of formula (Ia) above; and, where appropriate, (B) reacting such 5-substituted pyrimidine compound with an appropriate derivatizing agent (e.g., an alkyl or aryl acid halide, carbamoyl halide, alkyl halide, sulfonyl halide or phosphoryl halide or trialkylsilylhalide) or an appropriate isocyanate, or sequentially first with phosgene or a phosgene equivalent and then with an appropriate amine to produce the desired compound.

Typically, about 1–2 equivalents of an appropriate base (such as lithium diisopropyl amide or n-butyl lithium) and a substituted pyrimidine compound, as defined above, in a solvent (such as ethylene glycol dimethyl ether, tetrahydrofuran, diethyl ether or the like) are combined at a temperature of between about −100° C. and about 0° C. After suitable blending, about 1–2 equivalents of the pyrimidine carboxaldehyde are generally added.

This reaction mixture is typically agitated and slowly warmed to ambient temperature (about 25° C.) over a period of 1–24 hours. The reaction may be quenched with an aqueous solution and the 5-substituted pyrimidine compound so produced may be recovered by conventional techniques (such as extraction, filtration and the like) and purified by known methods, e.g., flash chromatography.

In the second step, the 5-substituted pyrimidine compound of formula (Ia), in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as an alkyl or aryl acid halide, carbamoyl halide, alkyl halide, sulfonyl halide or phosphoryl halide or trialkylsilylhalide) is then added and the mixture agitated until the reaction is complete. The reaction may be quenched by the addition of an aqueous solution, and the products recovered by conventional techniques, such as extraction, filtration and the like. The product so recovered may then be purified by conventional techniques such as flash chromatography and the like.

Alternatively, in the second step, the 5-substituted pyrimidine compound in a suitable solvent (such as tetrahydrofuran, methylene chloride or the like) may be added to between about 2 and about 3 equivalents of an appropriate isocyanate. Between about 1 and about 10 mole percent of one or more appropriate catalysts, e.g., triethyl amine or dibutyl tin dilaurate, may be added and the reaction mixture agitated at a temperature between about 0° C. and 100° C. for an appropriate period (e.g., 2 to 24 hours). The product may be recovered by conventional techniques (such as extraction, filtration or the like) and may be purified by conventional techniques such as flash chromatography or the like.

The substituted pyrimidine starting materials are either commercially available or may be prepared by one of ordinary skill in the art employing methods such as those described in *Chemical and Pharmaceutical Bulletin*, Vol. 7, Page 297 (1959). The substituted pyrimidine carboxaldehyde starting materials are commercially available or may be prepared employing techniques such as those described in the *Journal of Heterocyclic Chemistry*, Vol. 29, page 467 (1992) or as described below.

The compositions of this invention comprise a compound of formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by post-emergent application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such as bentazone;

B. hormone herbicides, particularly the phenoxyalkanoic acids such as MCPA, MCPA-thioethyl, dichlorprop, 2,4,5-T, MCPB, 2,4-D,2,4-DB, mecoprop, trichlopyr, fluroxypyr, clopyralid, and their derivatives (e.g. salts, esters and amides);

C. pyrazole derivatives such as pyrazoxyfen, pyrazolate and benzofenap;

D. dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and termacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

\* These compounds are preferably employed in combination with a safener such as 2,2-dichloro-N,N-di-2-propenylacetamide (dichlormid).

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly-cofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sethoxydim, cycloxydim, sulcotrione, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazathapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, flurochloridone, quinchlorac and mefanacet;

BB. examples of useful contact herbicides include bipyridylium herbicides such as those in which the active entity is paraquat and those in which the active entity is diquat.

These formulations can be applied to the areas where control is desired by conventional methods. Dust and liquid compositions, for example, can be applied by the use of powerdusters, boom and hand sprayers and spray dusters. The formulations can also be applied from airplanes as a dust or a spray or by rope wick applications.

The following are examples of typical formulations:

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| Wettable powders: | |
| --- | --- |
| 70%: | 70 parts active compound |
| | 5 parts sodium dibutylnaphthylsulfonate |
| | 3 parts naphthalenesulfonic acid/phenolsulfonic acid/phenol-sulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25% | 25 parts active compound |
| | 4.5 parts calcium lignin sulfate |
| | 1.9 parts Champagne chalk/-hydroxyethyl cellulose (1:1) |
| | 8.3 parts sodium aluminum silicate |
| | 16.5 parts kieselguhr |
| | 46 parts kaolin |
| 10% | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
| --- | --- |
| 25% | 25 parts active substance |
| | 2.5 parts epoxidized vegetable oil |
| | 10 parts of an alkylarylsulfonate/fatty alcohol polyglycol ether mixture |
| | 57.5 parts xylene |

The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

Example 1

Preparation of 1-(4-trifluoromethylpyrimidin-5-yl)-1-(4-methoxypyrimidin-5-yl)-1-trimethylacetoxymethane (Compound No. 16)

A. Preparation of 2-chloro-4-methoxypyrimidine-5-carboxaldehyde 2,2,6,6-Tetramethylpiperidine (2.7 ml, 2.25 g, 16.0 mmol) was added to a solution of n-butyl lithium (n-BuLi) (10 ml, 16.0 mmol, 1.6M in hexanes) in tetrahydrofuran (THF) (100 ml) at −78° C. The solution was allowed to warm to 0° C. and stirred for 45 minutes, cooled to −78° C. and 2-chloro-4-methoxypyrimidine (726 mg, 5.04 mmol) in THF (20 ml) was added dropwise. The solution was then stirred for 1 hour. Then, ethyl formate (0.50 ml, 0.46 g, 6.2 mmol) in THF (20 ml) was added dropwise and the solution was stirred for 1.5 hours. The reaction mixture was quenched with acetic acid (HOAc) (conc.) at −78° C., diluted with water and extracted with ethyl acetate (EtOAc) (3 times). The combined extracts were washed with saturated brine, dried (MgSO$_4$), filtered and concentrated in vacuo to give 1.06 g of crude material. Preparative radial chromatography (SiO$_2$; hexane/EtOAc gradient elution) afforded 420 mg (48%) of 2-chloro-4-methoxypyrimidine-5-carboxaldehyde.

B. Preparation of 1-(4-trifluoromethyl-6-chloropyrimidin-5-yl)-1-(2-chloro-4-methoxypyrimidin-5-yl)methanol 4-Chloro-6-trifluoromethylpyrimidine (1.10 g, 6.02 mmol) in THF (15 ml) was added to a solution of lithium diisopropyl amide (LDA) (prepared from n-BuLi (3.7 ml, 5.9 mmol, 1.6M in hexanes) added to diisopropylamine (820 ul, 591 mg, 5.84 mmol) in THF (30 ml) at −78° C., allowing to warm to room temperature for 30 minutes, and re-cooling to −78° C.) at −78° C. The solution turned brown and was stirred for 10 minutes. Then 2-chloro-4-methoxypyrimidine-5-carboxaldehyde (0.96 g, 5.56 mmol) in THF (25 ml) was added dropwise and allowed to stir at −78° C. for 1 hour. The solution was quenched at −78° C. with 30% aqueous HOAc, diluted with water and extracted with EtOAc (3 times). The combined extracts were washed with brine (sat.), dried (MgSO$_4$), filtered and concentrated in vacuo to give 1.61 g of crude product. Preparative radial chromatography (SiO$_2$; hexane/EtOAc gradient elution) gave 190 mg (21% based on 530 mg of recovered starting material) of 1-(4-trifluoromethyl-6-chloropyrimidin-5-yl)-1-(2-chloro-4-methoxypyrimidin-5-yl)methanol.

C. Preparation of 1-(4-trifluoromethylpyrimidin-5-yl)-1-(4-methoxypyrimidin-5-yl)methanol 1-(4-trifluoromethyl-6-chloropyrimidin-5-yl)-1-(2-chloro-4-methoxypyrimidin-5-yl)methanol (0.21 g, 0.59 mmol) was stirred under a hydrogen atmosphere at room temperature with MgO (142 mg, 3.35 mmol, 6 equivalents), and 10% palladium on carbon (Pd/C) (25 mg, Degussa, 50% wet by weight). After 3 hours, an additional 30 mg of 10% Pd/C was added and the solution stirred for 4 hours, filtered over celite and concentrated in vacuo. Preparative radial chromatography (SiO$_2$; hexane/EtOAc gradient elution) afforded the desired product, 81 mg (48%) as an oil.

D. Preparation of 1-(4-trifluoromethylpyrimidin-5-yl)-1-(4-methoxypyrimidin-5-yl)-1-trimethylacetoxymethane Trimethylacetyl chloride (36 μl, 35.1 mg, 0.28 mmol, 3.2 equivalent) was added via syringe to a solution of 1-(4-trifluoromethylpyrimidin-5-yl)-1-(4-methoxypyrimidin-5-yl)methanol (25.1 mg, 0.0877 mmol), triethylamine (70 μl, 50.5 mg, 0.50 mmol, 5.7 equivalents) and dimethylaminopyridine (DMAP) (cat.) in toluene (5 ml) and the solution heated to reflux for 2 hours. The solution was cooled, diluted with $NaHCO_3$ (sat.), and extracted with EtOAc (3 times). The combined extracts were washed with brine (sat.), dried ($MgSO_4$), filtered and concentrated in vacuo. Preparative thin layer chromatography ($SiO_2$; hexane/EtOAc, 1:1) gave 26 mg of 1-(4-trifluoromethylpyrimidin-5-yl)-1-(4-methoxypyrimidin-5-yl)-1-trimethylacetoxymethane as a solid.

Example 2

Preparation of 1-(4-trifluoromethylpyrimidin-5-yl)-1-(4-methoxypyrimidin-5-yl)-1-benzyloxymethane (Compound No. 17)

1-(4-trifluoromethylpyrimidin-5-yl)-1-(4-methoxypyrimidin-5-yl)methanol (56 mg, 0.196 mmol) in THF (2.5 ml) was added dropwise to a suspension of NaH (12 mg, 0.40 mmol, 80% in mineral oil) in THF (0.5 ml) at ice-bath temperature and stirred for 45 minutes. NaI (56 mg, 0.37 mmol) was then added as a solid and benzyl chloride (50 μl, 54 mg, 0.90 mmol, 2.25 equivalent) via syringe. Dimethyl formamide (DMF) (0.5 ml) was added and the solution was allowed to warm to room temperature. When the reaction was complete, as determined by TLC ($SiO_2$; hexane/EtOAc, 1:1), it was quenched with 30% aqueous HOAc, diluted with water and extracted with EtOAc (3 times). The combined extracts were washed with brine (sat.), dried ($MgSO_4$), filtered and concentrated in vacuo to give 66 mg of crude material. Preparative thin layer chromatography ($SiO_2$; hexane/EtOAc, 1:1) afforded 39 mg of 1-(4-trifluoromethylpyrimidin-5-yl)-1-(4-methoxypyrimidin-5-yl)-1-benzyloxymethane as an oil.

Example 3

Preparation of 1,1-bis-(4-trifluoromethylpyrimidin-5-yl)-1-benzyloxymethane (Compound No. 9)

A. Preparation of 4-chloro-6-trifluoropyrimidine

Phenylphosphonic dichloride (107 ml) and 4-trifluoromethylpyrimidin-6-one (103 g) were heated at 130° C. under nitrogen for 30 minutes. The reaction was cooled to room temperature and the reaction flask was equipped with a short path distillation head. The bath temperature was raised to about 200° C. and the product distilled out of the reaction mixture. Fractional distillation of this material gave 80.8 g of 4-chloro-6-trifluoromethylpyrimidine as a colorless liquid (b.p.= 134°–136° C. @ 760 mm Hg).

B. Preparation of 4-chloro-5-formyl-6-trifluoromethylpyrimidine

To a solution of 4.2 g of diisopropylamine in 100 ml of dry THF at –75° C. under $N_2$ were added 14.3 ml of a 2.5M solution of n-BuLi in hexanes dropwise. After stirring at –76° C. for 20 minutes a solution of 5.0 g of 4-chloro-6-trifluoromethylpyrimidine in 20 ml THF was added dropwise while maintaining the temperature below –70° C. The resulting lithiopyrimidine was then cannulated into a solution of 1.4 g of ethyl formate in 10 ml of THF at –30° C. After about 20 minutes the reaction was quenched with 10% $KH_2PO_4$ (pH=3.5). The mixture was extracted with ether (3 times), and the combined organic layers were washed with brine, dried with magnesium sulfate, filtered and evaporated to yield 5.4 g of a brown oil. Chromatography on silica gel (dichloromethane/hexane, 1/1) yielded 1.4 g of 4-chloro-5-formyl-6-trifluoromethylpyrimidine as a yellow solid.

C. Preparation of 1,1-bis-(4-chloro-6-trifluoromethylpyrimid-5-yl)methanol

To a solution of 0.59 g of diisopropylamine in 20 ml THF at –65° C. under $N_2$ was added 3.1 ml of 1.6M of n-BuLi dropwise. The solution was stirred at –65° C. for 30 minutes before being chilled to –76° C. A solution of 4-chloro-5-formyl-6-trifluoromethylpyrimidine in 5 ml THF was then added dropwise while maintaining the temperature below –70° C. The solution was stirred at –78° C. for 30 minutes before being quenched with 10 ml of 10% $KH_2PO_4$ (pH= 3.5), extracted with ether (3 times), washed with brine, dried over magnesium sulfate, filtered and evaporated to yield 1.48 g of a viscous brown oil. Chromatography on silica gel using 9/1 hexane/ethylacetate as eluant afforded 472 mg of 1,1-bis-(4-chloro-6-trifluoromethylpyrimid-5-yl)methanol as a yellow solid.

D. Preparation of 1,1-bis-(4-trifluoromethylpyrimid-5-yl)methanol

To a solution of 0.44 g of 1,1-bis-(4-chloro-6-trifluoromethylpyrimid-5-yl)methanol in 4.0 ml methanol were added 0.246 g magnesium oxide and 66 mg of 10% Pd/C (50% wet, Degussa). The mixture was then shaken on a Parr hydrogenation apparatus for 6 hours under 50 psi of hydrogen. The palladium catalyst and excess magnesium oxide were removed by filtration through dicalite, and the methanol filtrate was concentrated in vacuo to afford 318 mg of 1,1-bis-(4-trifluoromethylpyrimid-5-yl)methanol as an orange oil.

E. Preparation of 1,1-bis-(4-trifluoromethylpyrimid-5-yl)-1-benzyloxymethane To a solution of 160 mg of 1,1-bis-(4-trifluoromethylpyrimidin-5-yl)methanol in 2 ml THF at –30° C. under $N_2$ was added a suspension of oil-free sodium hydride in 0.5 ml THF. This was allowed to warm to –20° C. and after a few minutes gas evolution ceased. The solution was again cooled to –30° C. and 91 mg benzyl bromide was added. The reaction was allowed to slowly warm to room temperature. The reaction mixture was combined with 20 ml ether, washed with brine, dried over magnesium sulfate, filtered and evaporated to yield 159 mg of a brown oil. This was chromatographed on silica gel using 10% EtOAc in hexane as the eluant to yield 88 mg of 1,1-bis-(4-trifluoromethylpyrimid-5-yl)-1-benzyloxymethane as an oil.

Example 4

Preparation of 1-(4-ethylpyrimidin-5-yl)-1-(4-methylpyrimidin-5-yl)methanol (Compound No. 15)

A. Preparation of 2-(allyloxycarbonyl)-1-(4-methylpyrimidin-5-yl)pentan-1,3-dione To 0.5 g of 4-methylpyrimidine-5-carboxylic acid in 6 ml toluene was added 0.364 g of triethylamine. The solution was cooled to about 0° C. and a solution of 0.393 g of ethyl chloroformate in 2 ml of toluene was added dropwise over 15 minutes. The reaction mixture was stirred at 0° C. for 45 minutes and the precipitated triethylamine hydrochloride was removed by filtration. To the cooled filtrate was added the magnesium enolate of allyl propionylacetate in 5 ml of toluene. (The magnesium enolate was generated by refluxing 0.56 g allyl propionylacetate in 5 ml of THF with 0.38 g Mg(OEt)$_2$ for two hours and removing the volatiles in vacuo.) The mixture was allowed to come to room temperature over 1 hour and stirred overnight. Ether (15 ml) was added followed by 10 ml aq. KH$_2$PO$_4$ (pH 3.5). The aqueous layer was extracted (3 times, 15 ml) with ether, and the combined organics dried (Na$_2$SO$_4$) and stripped to yield 695 mg of crude product. Purification of 2.1 g crude product (from combined preparations) was accomplished by chromatography on silica gel using dichloromethane-methanol (10/1) to yield 680 mg of 2-(allyloxycarbonyl)-1-(4-methylpyrimidin-5-yl)pentan-1,3-dione.

B. Preparation of 1-(4-methylpyrimidin-5-yl) pentan-1,3-dione

To a suspension of 6.6 mg of palladium diacetate (Pd (OAc)$_2$), triethylamine (226 mg), and formic acid (204 mg) in 2 ml THF was added 410 mg of 2-(allyloxycarbonyl)-1-(4-methylpyrimidin-5-yl)pentan-1,3-dione. The mixture was refluxed for 3.5 hours, cooled and partitioned between ethyl acetate and water. The organic layer was dried with magnesium sulfate, filtered and evaporated to yield 290 mg of 1-(4-methylpyrimidin-5-yl)pentan-1,3-dione as an amber liquid.

C. Preparation of 2-(dimethylaminomethylene)-1-(4-methylpyrimidin-5-yl)-pentan-1,3-dione To 181 mg of dimethylformamide dimethyl acetal was added 250 mg of 1-(4-methylpyrimidin-5-yl)pentan-1,3-dione. The mixture was stirred for 16 hours at room temperature and the volatiles removed by bulb-to-bulb distillation (80° C.; 0.01 mm Hg) to yield 278 mg of 2-(dimethylaminomethylene)-1-(4-methylpyrimidin-5-yl) pentan-1,3-dione as an oil.

D. Preparation of (4-ethylpyrimidin-5-yl)-4-methylpyrimidin-5-yl ketone

To a solution of 550 mg of 25% sodium ethoxide in 3 ml anhydrous ethanol was added 176 mg of formamidine acetate at 0° C. To this solution was added 380 mg of 2-(dimethylaminomethylene)-1-(4-methylpyrimidin-5-yl) pentane-1,3-dione. The mixture was stirred at 0° C. for 1 hour then warmed to reflux for 1 hour. The reaction was cooled, the volatiles removed in vacuo and the residue partitioned between ether and water. The organic layer was dried (MgSO$_4$) and concentrated to yield 410 mg of crude product. This was purified via chromatography on silica gel utilizing dichoromethane-methanol as eluant to yield 184 mg of (4-ethylpyrimidin-5-yl)-4-methylpyrimidin-5-yl ketone.

E. Preparation of 1-(4-ethylpyrimidin-5-yl)-1-(4-methylpyrimidin-5-yl)methanol To a solution of 63 mg of (4-ethylpyrimidin-5-yl)-4-methylpyrimidin-5-yl ketone in 1 ml EtOH chilled in an ice bath was added 7.4 mg of sodium borohydride. After stirring the solution for 30 minutes, 1 ml of EtOAc was added followed by 1 ml NaH$_2$PO$_4$ (pH=3.0). The mixture was stirred vigorously and the aqueous extracted with EtOAc (3 times). The organic layers were combined, dried (MgSO$_4$) and filtered through silica gel with EtOAc. The solvent was evaporated to yield 52 mg of pure 1-(4-ethylpyrimidin-5-yl)-1-(4-methylpyrimidin-5-yl)methanol.

F. Preparation of 1-(4-ethylpyrimidin-5-yl)-1-(4-methylpyrimidin-5-yl)-1-trimethylacetoxymethane To 3.2 mg of oil-free NaH was added 26 mg of 1-(4-ethylpyrimidin-5-yl)-1-(4-methylpyrimidin-5-yl)methanol in 1 ml THF at −30° C., followed by addition of 15 mg of pivaloyl chloride. After warming to room temperature and stirring for 1.5 hours, the reaction was quenched with 1 ml H$_2$O and extracted with ether (3 times). The combined organics were washed with brine, dried (MgSO$_4$) and evaporated to yield 30.7 mg of 1-(4-ethylpyrimidin-5-yl)-1-(4-methylpyrimidin-5-yl)-1-trimethylacetoxymethane as a yellow oil.

Example 5

Preparation of 1-(4-methylpyrimidin-5-yl)-1-(4-trifluoromethylpyrimidin-5-yl)methanol (Compound No. 6)

A. Preparation of 3-dimethylamino-1-(4-methylpyrimidin-5-yl)-2-propen-1-one

To a solution of 28.2 g of 5-acetyl-4-methylpyrimidine in 250 ml of a chilled 1:1 mixture of benzene and DMF was added 33.6 g of tert-butoxy-bis(dimethylamino)methane dropwise. The solution was stirred overnight at room temperature. The solvents were evaporated in vacuo to yield 36.2 g of 3-dimethylamino-1-(4-methylpyrimidin-5-yl)-2-propen-1-one as a brick-red solid.

B. Preparation of 2-(dimethylaminomethylene)-4,4,4-trifluoro-1-(4-methylpyrimidin-5-yl)-butan-1,3-dione To a solution of 30 g of 3-dimethylamino-1-(4-methylpyrimidin-5-yl)-2-propen-1-one in 270 ml of dichloromethane chilled in an ice bath was added 34.6 g of trifluoroacetic anhydride. The solution was allowed to warm to room temperature and stirred overnight. The volatiles were evaporated to yield 65.7 g of crude 2-(dimethylaminomethylene)-4,4,4-trifluoro-1-(4-methylpyrimidin-5-yl)-butan-1,3-dione as a viscous brown oil.

C. Preparation of (4-methylpyrimidin-5-yl) 4-trifluoromethylpyrimidin-5-yl ketone To a cooled solution of 13 ml of 21 wt % sodium ethoxide and 45 ml of anhydrous ethanol was added 3.62 g formamidine acetate. To this chilled solution was added dropwise 10 g of 2-dimethylaminomethylene-4,4,4-trifluoro-1-(4-methylpyrimidin-5-yl)-butan-1,3-dione. The solution was stirred at 0° C. for 20 minutes, at room temperature for 30 minutes, then at reflux for 45 minutes. After cooling for 1 hour, the ethanol was stripped from the mixture, 250 ml of dichloromethane was added and washed with 100 ml water. The organic layer was dried with magnesium sulfate, filtered and evaporated to yield 2.94 g of crude of (4-methylpyrimidin-5-yl)-4-trifluoromethylpyrimidin-5-yl ketone as a viscous brown oil. This material can be purified further by chromatography on silica gel using hexane-ethylacetate (1:1) as the eluant.

D. Preparation of 1-(4-methylpyrimidin-5-yl)-1-(4-trifluoromethylpyrimidin-5-yl)methanol To a cooled solution of 300 mg of (4-methylpyrimidin-5-yl)-4-trifluoromethylpyrimidin-5-yl ketone in 4.5 ml of ethanol (EtOH) was added 30 mg of sodium borohydride in 1 ml EtOH dropwise over a period of 20 minutes. After stirring at 0°–5° C. for another 10 minutes, ethylacetate (25 ml) and 15 ml of 10% KH$_2$PO$_4$ (pH=3) were added followed by vigorous stirring. The layers were separated and the aqueous extracted twice with dichloromethane-methanol (10:1). The organic layers were combined, dried (MgSO$_4$) and stripped to yield 183 mg of 1-(4-methylpyrimidin-5-yl)-1-(4-trifluoromethylpyrimidin-5-yl)methanol.

Example 6

Employing processes similar to those described above, additional compounds, as listed in Table I were prepared.

TABLE 1

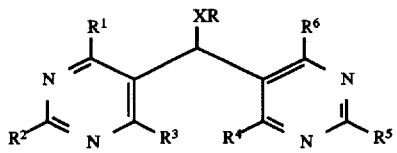

| Comp. No. | X | R | R$^1$ | R$^2$ | R$^3$ | R$^4$ | R$^5$ | R$^6$ |
|---|---|---|---|---|---|---|---|---|
| 1 | O | H | OCH$_3$ | Cl | H | H | Cl | OCH$_3$ |
| 2 | O | H | OCH$_3$ | H | H | H | H | OCH$_3$ |
| 3 | O | C(O)C(CH$_3$)$_3$ | OCH$_3$ | H | H | H | H | OCH$_3$ |
| 4 | O | Benzyl (Bz) | CF$_3$CF$_3$ | H | H | H | H | CH$_3$ |
| 5 | O | H | CF$_3$CF$_3$ | H | H | H | H | CH$_3$ |
| 6 | O | H | CF$_3$ | H | H | H | H | CH$_3$ |
| 7 | O | Bz | CF$_3$ | H | H | H | H | CH$_3$ |
| 9 | O | Bz | CF$_3$ | H | H | H | H | CF$_3$ |
| 10 | O | 4-fluoro-Bz | CF$_3$ | H | H | H | H | CF$_3$ |
| 11 | O | C(O)C(CH$_3$)$_3$ | CF$_3$CF$_3$ | H | H | H | H | CH$_3$ |
| 12 | O | C(O)N(CH$_2$CH$_3$)$_2$ | CF$_3$ | H | H | H | H | CH$_3$ |
| 13 | O | C(O)N(CH$_2$CH$_3$)$_2$ | CH$_3$ | H | H | H | H | CH$_2$CH$_3$ |
| 14 | O | C(O)C(CH$_3$)$_3$ | CH$_3$ | H | H | H | H | CF$_3$ |
| 15 | O | C(O)C(CH$_3$)$_3$ | CH$_3$ | H | H | H | H | CH$_2$CH$_3$ |
| 16 | O | C(O)C(CH$_3$)$_3$ | OCH$_3$ | H | H | H | H | CF$_3$ |
| 17 | O | Bz | OCH$_3$ | H | H | H | H | CF$_3$ |

HERBICIDAL SCREENING TESTS

The compounds listed in the foregoing tables were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

Pre-Emergence Herbicidal Screening Test

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

For the screening test results shown in Table II, the grass weeds planted were green foxtail (*Setaria viridis*) ("SETVI"), wild oat (*Avena fatua*) ("AVEFA"), barnyardgrass (*Echinochloa crusgalli*) ("ECHCG"). Broadleaf weeds utilized were wild mustard (*Sinapis arvensis*) ("SINAR"), velvetleaf (*Abutilon theophrasti*) ("ABUTH") and morningglory (Ipomoea spp.) ("IPOSS"). Additionally, yellow nutsedge (*Cyperus esculentus*) ("CYPES"), nutlets were sown.

For the screening tests results shown in Table III, the grass weeds planted were SETVI; AVEFA; ECHCG; blackgrass, slender foxtail (*Alopecurus myosuroides*); broadleaf signalgrass (*Brachiaria platyphylla*); rigid ryegrass (*Lolium rigidum*); fall panicum (*Panicum dichotomiflorum*); giant foxtail (*Setari faberi*); and Johnsongrass (*Sorghum halepense*). The average control achieved against these grass species ("AVG") is indicated in Table III. The broadleaf weeds planted were ABUTH; redroot pigweed (*Amaranthus retroflexus*); common lambsquarters (*Chenopodium album*); catchweed bedstraw (*Galium aparine*); ivyleaf morningglory (*Ipomoea hederacea*); scentless chamomile (*Matricaria perforata*); common purslane (*Portulaca oleracea*); and common cocklebur (*Xanthium strumarium*). The average control achieved against these broadleaf species ("AVB") is indicated in Table III. CYPES nutlets were also sown.

Solutions of the test compounds were prepared by weighing out an appropriate amount of the test compound to provide the application rates given in Tables II and III [kilograms (acid equivalent) per hectare (kg/ha)], then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha or 748 L/ha with the application rate being between 0.125 kg/ha and 0.65 kg/ha, as indicated. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The control ratings range from 0 to 100 percent, where 0 represents no effect with growth equal to the untreated control and where 100 represents complete kill.

TABLE II

| Comp. No. | Rate (kg/ha) | AVEFA | ECHCG | SETVI | ABUTH | IPOSS | SINAR | CYPES |
|---|---|---|---|---|---|---|---|---|
| 1 | 0.5 | 0 | 10 | 0 | 0 | 0 | 0 | 0 |
| 2 | 0.5 | 0 | 0 | 0 | 0 | 0 | 0 | 0 |
| 3 | 0.5 | 0 | 15 | 20 | 5 | 10 | 0 | 0 |
| 5 | 0.65 | 20 | 10 | 30 | 5 | 5 | 0 | 0 |
| 6 | 0.45 | 0 | 0 | 0 | 0 | 0 | 0 | 0 |

TABLE III

| Comp. No | Rate (kg/ha) | AVG | AVB | CYPES |
|---|---|---|---|---|
| 4 | 0.125 | 55 | 63 | 0 |
| 7 | 0.125 | 80 | 76 | 10 |
| 9 | 0.250 | 84 | 71 | 0 |
| 10 | 0.250 | 85 | 71 | 60 |
| 11 | 0.250 | 87 | 57 | 25 |
| 12 | 0.250 | 59 | 65 | 25 |
| 13 | 0.125 | 4 | 27 | 0 |
| 14 | 0.250 | 67 | 51 | 15 |
| 15 | 0.125 | 52 | 15 | 0 |
| 16 | 0.125 | 56 | 48 | 0 |
| 17 | 0.125 | 68 | 58 | 0 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of formula (I), or an N-oxide thereof:

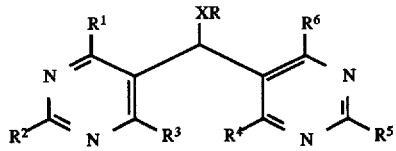

(I)

wherein:

$R^1$, $R^2$, $R^3$, $R^4$, $R^5$ and $R^6$ are each independently hydrogen, halogen, $C_1$–$C_6$ alkyl, $C_2$–$C_6$ alkenyl, $C_2$–$C_6$ alkynyl, ($C_1$–$C_6$)alkyl($C_3$–$C_6$)cycloalkyl, nitro, cyano, hydroxy, thiocyano, —N($R^7$)($R^8$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(Z)—$R^9$ or —S(O)$_m$—$R^{10}$, wherein $R^7$ and $R^8$ are each independently $C_1$–$C_6$ alkyl, $C_1$–$C_6$ alkylthio or $C_1$–$C_6$ alkoxy, $R^9$ and $R^{10}$ are each independently hydrogen, $C_1$–$C_6$ alkyl or phenyl, Z is oxygen or sulfur and m is 0, 1 or 2;

X is oxygen or sulfur;

R is hydrogen, hydrocarbyl, hydrocarbyl substituted with one or more of halogen or $C_1$–$C_6$ alkoxy or R is of the formula —C(Y)—$R^{11}$, —C(O)—C(O)—$R^{11}$, —S(O)$_2$—$R^{11}$, —P(Y)($R^{12}$)($R^{13}$) or —Si($R^{14}$)($R^{15}$)($R^{16}$); wherein Y is oxygen or sulfur;

$R^{11}$ is hydrocarbyl, substituted hydrocarbyl, hydrocarbyloxy, substituted hydrocarbyloxy, hydrocarbyl-S—, substituted hydrocarbyl-S— or is of the formula —N($R^{17}$)($R^{18}$), wherein $R^{17}$ and $R^{18}$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl ($C_1$–$C_6$)alkyl, hydroxycarbonyl($C_1$–$C_6$)alkyl, or N($R^{19}$)($R^{20}$) wherein $R^{19}$ and $R^{20}$ are each independently hydrogen, $C_1$–$C_6$ alkyl or phenyl;

or $R^{17}$ and $R^{18}$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolodine ring, any of which may be optionally substituted with $C_1$–$C_6$ alkyl;

$R^{12}$ and $R^{13}$ are each independently $C_1$–$C_6$ alkyl, $C_1$–$C_6$ alkylthio or $C_1$–$C_6$ alkoxy;

$R^{14}$, $R^{15}$ and $R^{16}$ are each independently $C_1$–$C_6$ alkyl, $C_1$–$C_6$ alkoxy, $C_1$–$C_6$ haloalkyl, aryl or arylalkyl;

with the proviso that when $R^1$ and $R^6$ are chloro and $R^2$, $R^3$, $R^4$ and $R^5$ are methoxy then R is not hydrogen;

with the further proviso that when $R^1$ and $R^4$ are chloro and $R^2$, $R^3$, $R^5$, and $R^6$ are methoxy then R is not hydrogen;

with the further proviso that when $R^3$ and $R^6$ are chloro and $R^1$, $R^2$, $R^4$ and $R^5$ are methoxy, then R is not hydrogen;

with the further proviso that when R 3 and R 4 are chloro and $R^1$, $R^2$, $R^5$ and $R^6$ are methoxy, then R is not hydrogen;

or an agriculturally acceptable salt thereof.

2. An herbicidal composition comprising an herbicidally effective amount of a compound according to claim 1, or an agriculturally acceptable salt thereof, and an agriculturally acceptable carrier therefor.

3. A method for controlling undesirable vegetation comprising applying to an area where control is desired an herbicidally effective amount of a compound according to claim 1, or an agriculturally acceptable salt thereof.

* * * * *